(12) United States Patent
Seltzer et al.

(10) Patent No.: US 6,379,150 B1
(45) Date of Patent: Apr. 30, 2002

(54) DENTAL HANDPIECE FILTER UNIT

(76) Inventors: Alan Seltzer, 707 Larchmont Rd., Elmira, NY (US) 14901; Mark Friedman, 133 Holden Rd., Pine City, NY (US) 14871

( * ) Notice: Subject to any disclaimer, the term of this patent is extended or adjusted under 35 U.S.C. 154(b) by 0 days.

(21) Appl. No.: 09/670,252

(22) Filed: Sep. 26, 2000

(51) Int. Cl.$^7$ ............................. A61C 1/10; A61C 17/00
(52) U.S. Cl. ......................... 433/80; 433/82; 433/126
(58) Field of Search ............................. 433/80, 81, 82, 433/83, 84, 85, 86, 87, 126

(56) References Cited

U.S. PATENT DOCUMENTS

| | | | |
|---|---|---|---|
| 3,521,359 A | * 7/1970 | Harris | 433/126 |
| 3,921,296 A | * 11/1975 | Harris | 433/126 |
| 4,950,159 A | 8/1990 | Hansen | 433/80 |
| 5,204,004 A | 4/1993 | Johnston et al. | 210/651 |
| 5,370,534 A | * 12/1994 | Wolf et al. | 433/80 |
| 5,474,451 A | 12/1995 | Dalrymple et al. | 433/80 |
| 5,554,025 A | 9/1996 | Klnsel | 433/80 |
| 5,556,279 A | 9/1996 | Wolf et al. | 433/82 |
| 5,709,545 A | * 1/1998 | Johnston et al. | 433/80 |
| 5,716,210 A | 2/1998 | Novak | 433/82 |
| 5,897,317 A | 4/1999 | Hansen | 433/132 |
| 5,908,296 A | 6/1999 | Kipke et al. | 433/80 |
| 5,961,326 A | 10/1999 | Johnston et al. | 433/80 |
| 5,971,757 A | 10/1999 | Seltzer et al. | 433/80 |

* cited by examiner

*Primary Examiner*—John J. Wilson
(74) *Attorney, Agent, or Firm*—Brown & Michaels, PC

(57) ABSTRACT

The present invention provides a dental handpiece filter unit containing a filter that minimizes the exposure of patients to pathogens found in the dental water supply lines while promoting frequent replacement of DUWL filters by providing a disposable microfiltration filter that is easily replaced at low cost. A disk or membrane type filter is placed in a disconnectable autoclavable filter unit in the handle of an existing design dental instrument such that the form and function of the dental instrument are not adversely affected. The handpiece filter unit, which fits in-line between the dental unit and the water line fitting, includes a waterline connector, a filter-housing unit, and a handpiece connector. Each of these components is connected to each other via plastic tubing. Specifically, the air and exhaust lines run from the waterline connector to the handpiece connector, circumventing the filter unit. The water line, however, passes from the waterline connector, through the filter unit where the water is filtered, and into the handpiece connector. This unique design of three distinct compartments which are autoclavable, connected by autoclavable plastic piping makes the handpiece filter unit both economical to produce and ideal for its intended use.

17 Claims, 3 Drawing Sheets

DENTAL HANDPIECE FILTER UNIT

BACKGROUND OF THE INVENTION

1. Field of the Invention

This invention relates to a handpiece filter unit for a dental instrument designed for use inside a patient's mouth, and in particular, to an in-line disk filter and filter handpiece for the type of a dental instrument that delivers water within a patient's mouth.

2. Description of Related Art

Dentists often use instruments, such as handpieces, ultrasonic scalers, or syringes, that deliver water and air into a patient's mouth during the course of a dental procedure. A pressing concern in the use of such instruments is the risk of infection created by disease-causing microorganisms (pathogens) which build up over the course of time in both the dental unit water line (DUWL) that supplies the instrument and in the tips of the instruments themselves. The DUWL typically extends from the dental instrument to a water source originating either from the municipal water supply or from bottled supplies within the dentist's office. Contamination is particularly promoted within DUWL's because the water in these lines is frequently stagnant since the water flows only when the instrument is in use. There are two principal sources of instrument contamination. The first source of contamination is the pathogens found in the water supply that attach themselves to the walls of the DUWL's. The second source of contamination is the pathogens that are sucked into the instrument and DUWL due to backflow from the patient's mouth (the point of use).

The way in which DUWL's become contaminated is well known. Basic principles of fluid mechanics dictate that zones of stagnation form around the perimeter of a DUWL. These zones exist because the velocity of flowing water is zero at the walls of the tube. In the absence of agitation, microorganisms breed and flourish in the form of thin biofilms. Found among these organisms are pathogens such as legionella, pseudomonas, and mycobacteria. Biofilms occasionally break off from the walls of the DUWL and float downstream into a patient's mouth, greatly increasing the risk of infection. Backflow is another significant source of pathogens. Backflow occurs when some of an infected patient's fluids are sucked into the tip of the instrument, eventually contaminating the entire instrument. The risk of pathogen transmission and infection becomes especially significant when immuno-compromised patients, such as HIV-positive victims and cancer victims, are exposed to water from the DUWL.

Conventional methods of sterilization fail to prevent the breeding and growth of pathogens in DUWL's. Simple liquid flushing does not solve the problem, as the biofilms are generally unaffected by flowing liquid. Likewise, flushing with biocide or other decontaminants is ineffective as many organisms are resistant to these chemical treatments. Finally, use of purified water sources to minimize the contaminants in the entering water flow is not a viable solution because pathogens multiply rapidly once the seal on the water supply is opened.

Autoclaving is the most effective method of contaminant control. Although the instrument or instrument head usually is detachable and therefore suitable for autoclaving, the DUWL's generally are not detachable and are too long and unwieldy to be autoclaved. In addition, DUWL's usually are not designed to withstand this sort of treatment.

Several attempts at filtering water flowing via the DUWL through the instrument have proven cumbersome and economically inefficient.

In Hansen, U.S. Pat. No. 4,950,159, a disposable cartridge filter is disclosed which uses activated charcoal in the filter. This material is ill suited for filtering the water in the DUWL because the pore size of activated charcoal is too large to effectively filter out pathogens.

In Johnston, et. al, U.S. Pat. No. 5,204,004, the filter is not placed in the handle and the DUWL must be cut in order to install a new filter. These limitations are likely to make the instrument cumbersome for a dentist to use and time-consuming to replace. Due to the position of the filter, it does not solve the backflow problem without the use of a separate check-valve or the chemical disinfection of the DUWL between patients, thus adding cost and complexity to its use.

In Dalrymple, et. al, U.S. Pat. No. 5,474,451, a series of air/water filter housings are disclosed. However, the filtering mechanisms entail a multivalent iodine resin/halogen scavenging system. The cost of this scheme precludes frequent replacement and disposal of the filter cartridges. In addition, several of the preferred water treatment embodiments require a filter manifold approximately two inches in length which makes the dental instrument unwieldy. This unwieldiness undercuts the purpose of dental instruments designed for easy manipulation within a patient's mouth. This approach also introduces chemicals into the water which is delivered to the patient's mouth.

In Wolf, et. al, U.S. Pat. No. 5,556,279, the filter is based on a chemical method of decontamination, thus making the filters more expensive and not amenable to frequent disposal. As in Dalrymple, this approach also introduces chemicals into the water which is delivered to the patient's mouth.

In Kinsel, U.S. Pat. No. 5,554,025, the filter is placed very close to the tip of the instrument, in close proximity to the point of use. While this is beneficial for decontamination purposes, it can make the instrument unwieldy due to the location of the filter housing. In addition, the proposed filter design is not suitable for the actual physical orientation of liquid and air tubes in a DUWL. This approach requires the entire filter and housing to be disposed of when changing filters, thus adding to cost. Also, while Kinsel's filter arrangement might be suitable for a dental syringe, it might not be suitable for a handpiece due to the greater volume of water required to cool a handpiece.

Novak, U.S. Pat. No. 5,716,210, is similar to the present invention in that there is a section inserted between the DUWL and the dental unit, which contains a filter. In Novak, each of the conduits pass through the filter cartridge, which makes the cartridge more complicated to machine and produce. The filter cartridge is disposable, not autoclavable.

In Hansen, U.S. Pat. No. 5,897,317, the filter cartridge is disposable. The filter cartridge filters, water, air, and the exhaust through a combination of filters. There are three cavities in the filter cartridge. The first cavity holds a filter for filtering air, the second cavity holds a filter for filtering water, and the third cavity holds a filter for filtering the exhaust. This configuration of the filter cartridge is potentially complicated and expensive to manufacture.

In Kipke et al., U.S. Pat. No. 5,908,296, a syringe includes a replaceable device for purifying water. The water-purifying device consists of disinfecting iodide beads in the tip of the syringe.

In Johnston et al., U.S. Pat. No. 5,961,326, a one-way valve protects a dental patient from bacteria. The valve is preferably combined with a filter. The valve is installed in the water line itself, and the waterline must be cut each time a new valve is installed. This limitation is likely to make the instrument cumbersome for a dentist to use and time-consuming to replace.

U.S. Pat. No. 5,971,757, by the present inventors, discloses a disk or membrane type filter placed in an autoclavable filter unit in the handle of an existing design dental instrument such that the form and function of the dental instrument are not adversely affected. The filter unit, which fits in-line between the dental unit and the water line fitting, includes two portions that are detachably connected by an annular sleeve. When connected, a recess between the portions forms a recess that holds a micro filtration disk filter for filtering water that flows through the dental instrument before it reaches a patient's mouth. This design, while entirely functional, can be difficult and expensive to manufacture, because of the need to machine passages through a solid body for each fluid.

The presence and potential harm of pathogens in DUWL's and dental instruments are well documented and the American Dental Association has called for a solution.

SUMMARY OF THE INVENTION

The present invention provides a dental handpiece filter unit containing a filter that minimizes the exposure of patients to pathogens found in the dental unit water lines (DUWL) while promoting frequent replacement of DUWL filters, by providing a disposable microfiltration filter that is easily replaced at low cost. A disk or membrane type filter is placed in a disconnectable autoclavable filter unit in the handle of an existing design dental instrument such that the form and function of the dental instrument are not adversely affected. The handpiece filter unit, which fits in-line between the dental unit and the water line fitting, includes a waterline connector, a filter-housing unit, and a handpiece connector. Each of these components is connected to each other via plastic tubing. Specifically, the air and exhaust lines run from the waterline connector to the handpiece connector, circumventing the filter-housing unit. The water line, however, passes from the waterline connector, through the filter-housing unit where the water is filtered, and into the handpiece connector. This unique design of three distinct components which are autoclavable, and connected by autoclavable plastic tubing makes the handpiece filter unit both economical to produce and ideal for its intended use.

DETAILED DESCRIPTION OF THE INVENTION

The present invention minimizes pathogen exposure by preventing pathogens within the dental unit water line (DUWL) from migrating to the patient's mouth and by permitting sterilization of filter-housing unit. Those pathogens in locations not subject to sterilization are filtered before reaching the patient's mouth. The water flowing in from the DUWL is filtered and both parts of the filter housing are readily autoclavable. In addition, the invention prevents pathogens from a patient's mouth from migrating into the DUWL. The fact that each part of the handpiece filter unit can be manufactured independently allows the unit to be manufactured at a low cost. In addition, each part of the handpiece filter unit is independently autoclavable, contributing to the overall sterility of the device during use.

Figure 1:
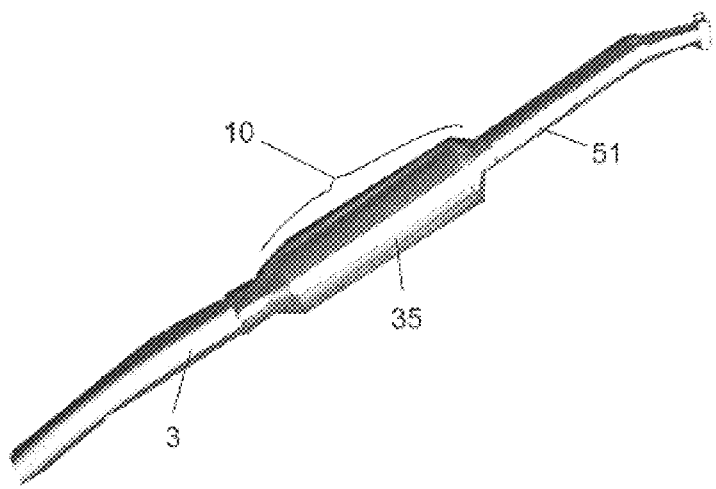
FIG. 1 shows a side view of the invention in its housing, attached to a dental handpiece and water line.

Referring to FIG. 1, the handpiece filter unit (10) of the invention is connected to the waterline (3) and a handpiece (51), in this case a dental handpiece, although it will be understood that the invention is equally applicable to syringes or ultrasonic scalers, or any other dental instrument having a water supply. A housing (35) covers the handpiece filter unit (10) to make it easier to maneuver during use.

Figure 2A:
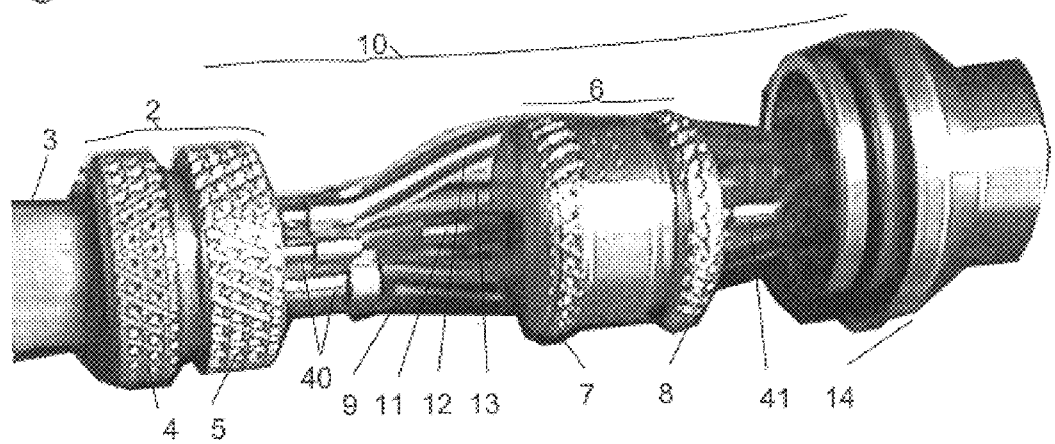
FIGS. 2A and 2B show a side view of the dental handpiece filter and the tubing of the present invention, from opposite sides.
Figure 2B:
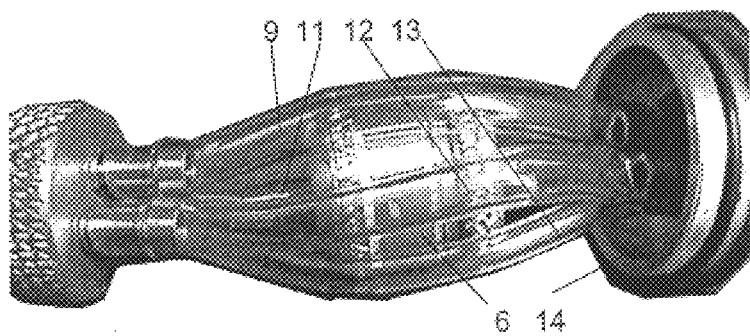

FIGS. 2A and 2B shows the components which are located within the handpiece filter unit (10). The handpiece filter unit (10) connects to a water line connector (2), which is standardized to allow interconnection of various instruments to the dental unit waterline (DUWL) (3). The waterline connector (2) includes a first section (4) and a second section (5). The first section is reversibly attached to the waterline (3), and also to the second section (5).

In the embodiment shown in the drawing, four pieces of tubing (9), (11), (12), and (13) are attached to the waterline connector (2). All of the tubing described herein is preferably plastic, reusable and autoclavable. Although four pieces of tubing are described in this example, any number of pieces of tubing necessary for transfer of air, and/or exhaust to and from the dental instrument would not deviate from the spirit of the invention as long as one of the pieces of tubing was available to deliver fluid to the filter-housing unit (6). Tubing (11), which is the first half of the tubing through which water flows, transmits water from the waterline connector (2) into a filter-housing unit (6). The filter-housing unit (6) is divided into a first section (7) and a second section (8), which are disconnectable. An additional piece of tubing (41) connects the filter-housing unit (6) to the handpiece connector (14). The handpiece connector (14) connects the handpiece filter unit (10) to the handpiece.

Tubing adaptors (40), preferably made of brass, are preferably used to connect each of the pieces of tubing described herein to the components of the handpiece filter unit (10).

The handpiece filter unit (10) is completely disconnectable. Each piece, including the tubing, can be disconnected from the others and independently autoclaved. Therefore, the instrument is easy and cost-effective to manufacture, as well as simple to sterilize.

FIG. 2B is a view of the invention from the other side, relative to FIG. 2A. This view shows tubing (9), (12), and (13) in the foreground and the filter-housing unit (6) in the background. These three pieces of tubing (9), (12), and (13), circumvent the filter-housing unit (6) to enter the handpiece connector (14).

Figure 3:
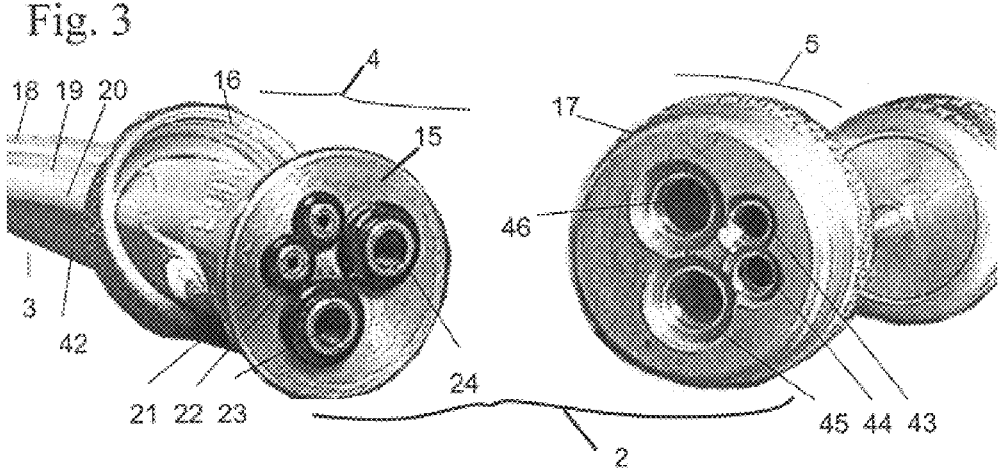
FIG. 3 shows an open view of one type of waterline connector for the present invention.

Referring to FIG. 3, the first section (4) of the waterline connector (2) typically includes a connector insert (15) which connects to the various fluid conduits discussed below, and a threaded or bayonet-equipped sleeve (16), which surrounds the insert (15) and connects it firmly to the mating threads (17) on the second section (5) of the waterline connector (2). Alternatively, the coupling between the connector insert (15) and the second section (5) of the waterline connector (2) is achieved using protruding tubular portions that fit snugly into corresponding recesses in a male-female connection.

Water flows into the instrument through a dental unit water line (DUWL) (3), flowing left to right in FIG. 1. Water is typically used both to cool the tip of the dental instrument and to clear debris formed at a point of use (not shown) within a patient's mouth. The waterline conduit (42) allows water transfer through the dental instrument. Other conduits might include a line (18) to supply pressurized air to power the instrument, a conduit (19) to carry air exhaust away, and a conduit (20) to provide air for the aeration of water used within the patient's mouth. This four-conduit arrangement is currently the most widely used in dentistry. An optical fiber line (not shown) is sometimes provided as well, to supply illumination at the tip of the instrument. All of these are coupled to connector fittings such as (21), (22), (23) and (24) through mating sockets (43), (44), (45), and (46), respectively in the second section (5) of the waterline connector (2), and then up through the handpiece filter unit (10) as needed.

It will be understood that the number and function of these conduits, the number of fittings on the waterline connector (2), the matching sockets on the second section of the waterline connector (2), and the number of pieces of tubing will vary according to the individual dentist's equipment. So long as there is a water line which requires filtering, adapting the invention to the arrangement of conduits is within the ability of one skilled in the art.

Figure 4A:
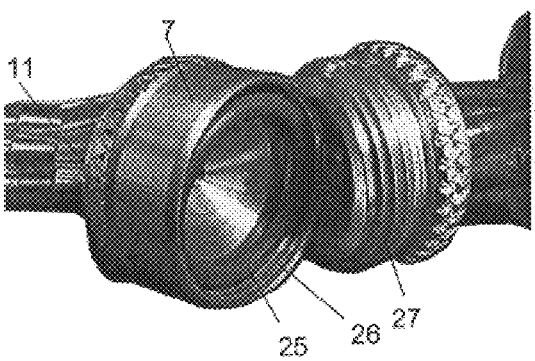
FIG. 4A shows an open view of the filter-housing unit of the present invention.
Figure 4B:
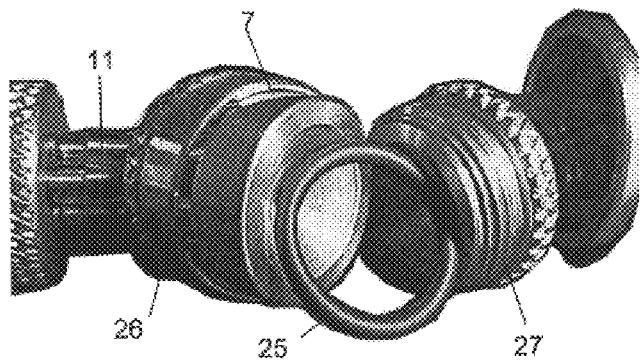
FIG. 4B shows an open view of the filter-housing unit of the present invention with the o-ring removed.
Figure 5A:
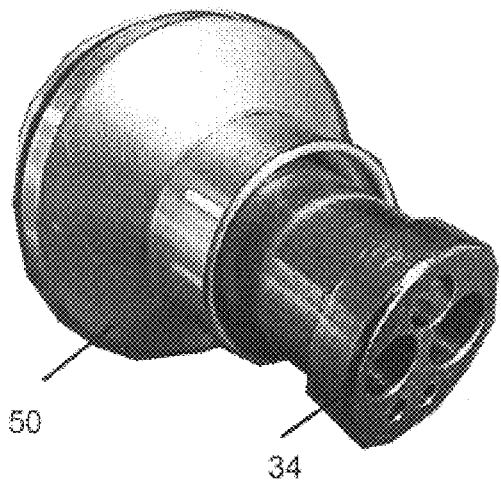
FIG. 5A shows a front view of the handpiece connector of the present invention.
Figure 5B:
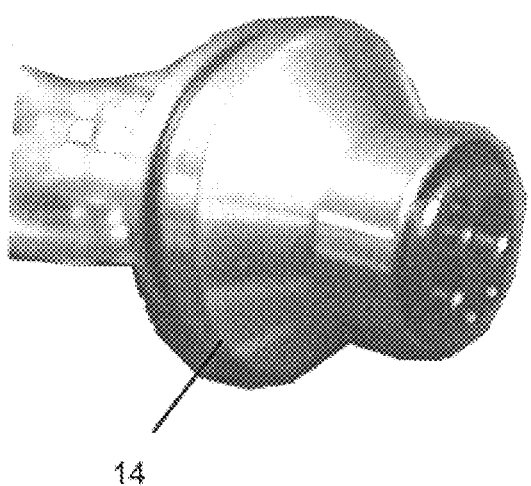
FIG. 5B shows a front view of the handpiece connector of the present invention.
Figure 5C:
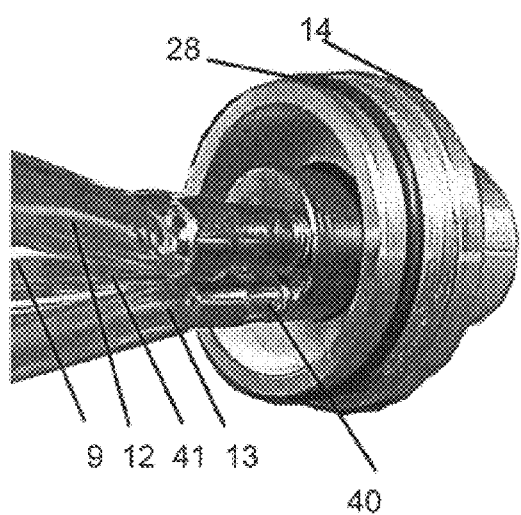
FIG. 5C shows a rear view of the handpiece connector of the present invention.
Figure 5D:
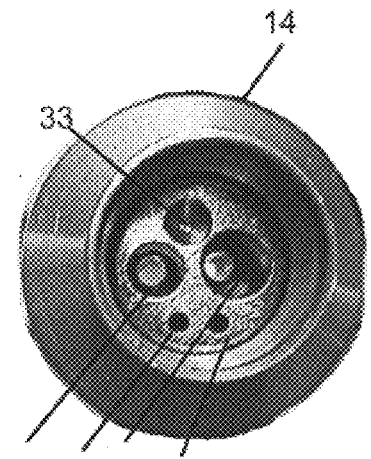
FIG. 5D shows detail of the end of the handpiece connector of the present invention.

Referring to FIGS. 4A and 4B, the first section (7) of the filter-housing unit (6) has a conduit for receiving the waterline tubing (11). The first section (7) is also adapted to hold an o-ring (25) snugly within it. The autoclavable o-ring (25) and a recess in the filter-housing unit (6) are preferably used to hold a microfiltration disk (not shown) rigid and in place during use. The microfiltration disk is made of autoclavable filter material such as polyethersulfone, and preferably has a pore size of at most 0.22 μm. Water preferably leaves the microfiltration disk with less than 200 colony forming units per milliliter (cfu/mL) at a minimum flow rate of 50 milliliters per minute (mL/min). The filter is preferably disposable and inexpensive, although it could be made of a material which can be sterilized and replaced if desired.

The first section (7) also preferably has internal threading (26). This internal threading (26) interfits with threading (27) on the second section (8) of the filter-housing unit (6), allowing the filter-housing unit (6) to be tightly sealed. Alternatively, the coupling between the first section (7) and the second section (8) of the filter-housing unit (6) is achieved using protruding tubular portions that fit snugly into corresponding recesses in a male-female connection.

Referring to FIGS. 5A through 5D, the handpiece connector (14) includes the conduits to carry exhaust away (29), to provide pressurized air to power the instrument (30), to provide water (31), and to provide air for the patients' mouth (32) for the tubing (9), (12), (41), and (13) respectively. In this example, there is also a fifth conduit (33) shown on the handpiece connector (14). The fifth conduit (33) is for an optical fiber line (not shown), to supply illumination at the tip of the instrument. The optical fiber line is not being utilized in this example. The conduits connect to the tubing preferably via tubing adaptors (40). In the example shown in the Figures, a midwest connector (34) is found on the handpiece connector (14). The handpiece attaches to the midwest connector (34) and is secured with a midwest nut (50). The midwest nut (50) preferably contains an o-ring (28) for a friction fit. Although a midwest connection is shown here, any connection between the handpiece connector (14) and the handpiece would not deviate from the teachings of the invention.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A filter unit for a dental instrument, said dental instrument having a fluid connector for supply of a plurality of fluids to the dental instrument, at least one of which fluids is to be filtered and at least one other of said fluids is not to be filtered, said connector being adapted to mate with a fluid connector on the fluid supply line, the filter unit comprising:

a) a waterline connector having a body adapted to mate with the fluid connector on the fluid supply line and a plurality of fluid connectors adapted to mate with tubing, one fluid connection for each fluid passing through the waterline connector;

b) a handpiece connector having a body adapted to mate with the fluid connector on the dental handpiece, and a plurality of fluid connectors adapted to mate with tubing, one fluid connection for each fluid passing through the handpiece connector;

c) at least one filter housing having a body with a central filter chamber, the body being separable into a first section and a second section at the filter chamber, such that a filter may be inserted into the filter chamber; the first section and the second section having fluid connections adapted to mate with tubing and passages for fluid connecting the fluid connections to the central filter chamber, such that fluid entering a fluid connection on the first section passes into the central filter chamber and exits from the fluid connection on the second section;

d) at least one length of flexible tubing, connecting a fluid connection on the waterline connector to a fluid connection on the first section of the filter housing;

e) at least one length of flexible tubing, connecting a fluid connection on the handpiece connector to a fluid connection on the second section of the filter housing;

f) at least one length of flexible tubing connecting a fluid connection on the waterline connector to a fluid connection on the handpiece connection;

such that for each fluid to be filtered, fluid from the fluid supply line passes through the waterline connector into a length of flexible tubing, through the filter housing, and through a length of flexible tubing to the handpiece connector, and then to the dental instrument; and for each fluid which is not filtered, fluid from the fluid supply line passes through the waterline connector into a length of flexible tubing to the handpiece connector, and then to the dental instrument.

2. The filter unit of claim 1, wherein each component of the filter unit is autoclavable.

3. The filter unit of claim 1, wherein at least one of the fluids which is not filtered is pressurized air to power the dental instrument.

4. The filter unit of claim 1, wherein at least one of the fluids which is not filtered is air exhaust away from the dental instrument.

5. The filter unit of claim 1, wherein one wherein at least one of the fluids is air for the aeration of water inside a mouth of a patient.

6. The filter unit of claim 5, in which the air for the aeration of water is a fluid which is not filtered.

7. The filter unit of claim 5, in which the air for the aeration of water is a fluid which is filtered.

8. The filter unit of claim 1, in which the fluid supply line has an optical fiber line to supply illumination to the dental instrument, the fluid connector on the fluid supply line has a fiber optic connector connected to the optical fiber line, and the fluid connector on the dental instrument has a fiber optic connector adapted to couple with the fiber optic connector on the fluid connector on the fluid supply line, the filter unit further comprising:
- a fiber optic connection on the waterline connector, adapted to couple with the fiber optic connector of the fluid connector of the fluid supply line;
- a fiber optic connection on the handpiece connector, adapted to couple with the fiber optic connector of the fluid connector of the handpiece; and
- a fiber optic line connecting the fiber optic connection of the waterline connector to the fiber optic connection of the handpice connector.

9. The filter unit of claim 1, in which at least one of the fluids which is filtered is water.

10. The filter unit of claim 1, further comprising a fluid-tight seal located between the first section and the second section of the filter housing.

11. The filter unit of claim 10, wherein the fluid-tight seal is an o-ring.

12. The filter unit of claim 1, further comprising a filter-unit housing connecting the waterline connector and the handpiece connector, and enclosing the filter housing and the tubing, such that when a dental instrument is connected to the handpiece connector, the filter-unit housing forms an extension of a handle of the dental instrument.

13. The filter unit of claim 1, wherein the handpiece connector comprises a midwest connector and a midwest nut to connect the filter unit to a handpiece.

14. The filter unit of claim 13, wherein the midwest nut comprises an o-ring for a friction fit.

15. The filter unit of claim 1, further comprising a filter in the filter chamber of the filter housing, such that the fluid passing through the fluid passageway is filtered by the filter in the filter chamber.

16. The filter unit of claim 15, in which the filter is a microporous disk.

17. The filter unit of claim 16, in which the filter has pores no larger than 0.22 $\mu$m.

* * * * *